United States Patent [19]
Heinemann et al.

[11] Patent Number: 5,633,267
[45] Date of Patent: May 27, 1997

[54] PYRIDYL-1,2,4-THIADIAZOLES AS PEST-CONTROL AGENTS

[75] Inventors: Ulrich Heinemann, Leichlingen; Ralf Tiemann, Leverkusen; Heinz-Wilhelm Dehne, Bonn, all of Germany

[73] Assignee: Bayer Aktiengesellschaft, Leverkusen, Germany

[21] Appl. No.: 433,414

[22] PCT Filed: Nov. 15, 1993

[86] PCT No.: PCT/EP93/03198

§ 371 Date: May 19, 1995

§ 102(e) Date: May 19, 1995

[87] PCT Pub. No.: WO94/12496

PCT Pub. Date: Jun. 9, 1994

[30] Foreign Application Priority Data

Nov. 26, 1992 [DE] Germany .................. 42 39 727.8

[51] Int. Cl.$^6$ .................. C07D 417/04; G01N 43/40
[52] U.S. Cl. .................. 514/342; 546/268.7
[58] Field of Search .................. 546/277, 268.7; 514/342

[56] References Cited

U.S. PATENT DOCUMENTS 3,736,328 5/1973 Wittenbrook et al. .
3,770,749 11/1973 Phillips .
5,166,165 11/1992 Kleefeld .................. 514/364

FOREIGN PATENT DOCUMENTS

| 0116515 | 8/1984 | European Pat. Off. . |
| 0273534 | 7/1988 | European Pat. Off. . |
| 0285565 | 10/1988 | European Pat. Off. . |
| 0486798 | 5/1992 | European Pat. Off. . |
| 1518150 | 3/1968 | France . |
| 9216527 | 1/1992 | WIPO . |

*Primary Examiner*—D. R. Wilson
*Attorney, Agent, or Firm*—Sprung Horn Kramer & Woods

[57] ABSTRACT

Fungicidal novel pyridyl-1,2,4-thiadiazoles of the formula

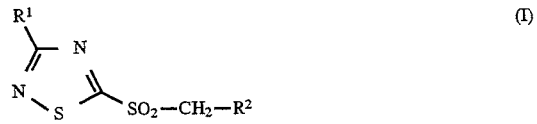

(I)

in which $R^1$ represents optionally substituted pyridyl, and $R^2$ represents optionally substituted aryl, and their preparation by oxidation of 5-arylalkylthio-1,2,4-thiadiazoles of the formula

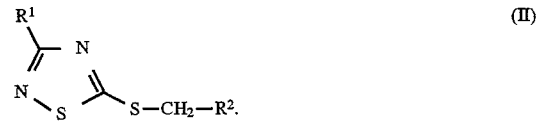

(II)

1 Claim, No Drawings

PYRIDYL-1,2,4-THIADIAZOLES AS PEST-CONTROL AGENTS

The present invention relates to novel pyridyl-1,2,4-thiadiazoles, to a process for their preparation and to their use as agents for combating pests.

It has already been disclosed that certain substituted heterocycles possess fungicidal properties (cf. DE-A 4 033 412). Thus, for example, 2-(3-trifluoromethyl-phenyl) 5-methylsulphonyl- 1,3,4-oxadiazole and 2-(4-fluorophenyl)-5-methylsulphonyl 1,3,4-oxadiazole can be used for combating fungi. The activity of these substances, however, is not completely satisfactory in all areas of application, especially at low application rates.

Novel pyridyl-1,2,4-thiadiazoles have now been found, of the formula

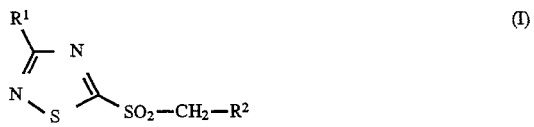

in which
R$^1$ represents optionally substituted pyridyl, and
R$^2$ represents optionally substituted aryl, and the acid addition salts and metal salt complexes thereof.

It has also been found that pyridyl-1,2,4-thiadiazoles of the formula (I) and the acid addition salts and metal salt complexes thereof are obtained if 5-arylalkylthio- 1,2,4-thiadiazoles of the formula

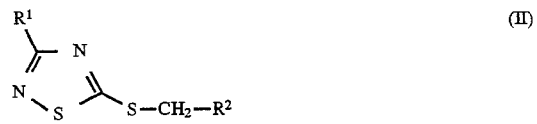

in which
R$^1$ and R$^2$ have the meanings given above are reacted with an oxidizing agent, optionally in the presence of a diluent, optionally in the presence of an acid-binding agent and optionally in the presence of a catalyst, and subsequently, if desired, an acid or a metal salt is added onto the compounds of the formula (I) thus obtained.

Finally it has been found that the novel pyridyl-1,2,4-thiadiazoles of the formula (I) and the acid addition salts and metal salt complexes thereof are very highly suited for combating pests.

Surprisingly, the substances according to the invention possess a considerably better activity against phytopathogenic microorganisms than 2-(3-trifluoromethylphenyl) 5-methylsulphonyl- 1,3,4-oxadiazole and 2-(4-fluorophenyl)-5-methylsulphonyl 1,3,4-oxadiazole, which are previously known active compounds which are similar in constitution and have the same mode of action.

A general definition of the pyridyl-1,2,4-thiadiazoles is given by the formula (I).

R$^1$ preferably represents 2-pyridyl, 3-pyridyl or 4-pyridyl, it being possible for each of these radicals to be monosubstituted to tetrasubstituted by identical or different substituents consisting of halogen, cyano, nitro, in each case straight-chain or branched alkyl, alkoxy or alkylsulphonyl having in each case 1 to 6 carbon atoms, in each case straight-chain or branched halogenoalkyl, halogenoalkoxy or halogenoalkylsulphonyl having in each case 1 to 6 carbon atoms and 1 to 13 identical or different halogen atoms, straight-chain or branched alkoxycarbonyl having 1 to 6 carbon atoms in the alkoxy group, straight-chain or branched alkoximinoalkyl having 1 to 6 carbon atoms in the alkoxy moiety and 1 to 6 carbon atoms in the alkyl moiety, and of phenyl which in turn may be monosubstituted to tetrasubstituted by identical or different substituents consisting of halogen and/or straight-chain or branched alkyl or alkoxy having in each case 1 to 6 carbon atoms and/or straight-chain or branched halogenoalkyl or halogenoalkoxy having in each case 1 to 6 carbon atoms and 1 to 13 identical or different halogen atoms.

R$^2$ preferably represents aryl having 6 to 10 carbon atoms, it being possible for each of these radicals to be monosubstituted to pentasubstituted by identical or different substituents consisting of halogen, cyano, nitro, in each case straight-chain or branched alkyl, alkoxy or alkylsulphonyl having in each case 1 to 6 carbon atoms, in each case straight-chain or branched halogenoalkyl, halogenoalkoxy or halogenoalkylsulphonyl having in each case 1 to 6 carbon atoms and 1 to 13 identical or different halogen atoms, straight-chain or branched alkoxycarbonyl having 1 to 6 carbon atoms in the alkoxy group, straight-chain or branched alkoximinoalkyl having 1 to 6 carbon atoms in the alkoxy moiety and 1 to 6 carbon atoms in the alkyl moiety, and of phenyl which in turn may be monosubstituted to pentasubstituted by identical or different substituents consisting of halogen and/or straight-chain or branched alkyl or alkoxy having in each case 1 to 6 carbon atoms and/or straight-chain or branched halogenoalkyl or halogenoalkoxy having in each case 1 to 6 carbon atoms and 1 to 13 identical or different halogen atoms.

R$^1$ particularly preferably represents 2-pyridyl, 3-pyridyl or 4-pyridyl, it being possible for each of these radicals to be monosubstituted to tetrasubstituted by identical or different substituents consisting of fluorine, chlorine, bromine, iodine, cyano, nitro, in each case straight-chain or branched alkyl, alkoxy or alkylsulphonyl having in each case 1 to 4 carbon atoms, in each case straight- chain or branched halogenoalkyl, halogenoalkoxy or halogenoalkoxysulphonyl having in each case 1 to 4 carbon atoms and 1 to 9 identical or different halogen atoms, such as fluorine, chlorine and/or bromine, of straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or of phenyl which in turn may be monosubstituted to trisubstituted by identical or different substituents consisting of fluorine, chlorine, bromine, straight-chain or branched alkyl or alkoxy having in each case 1 to 4 carbon atoms and/of straight-chain or branched halogenoalkyl or halogenoalkoxy having in each case 1 to 4 carbon atoms and 1 to 9 fluorine, chlorine and/or bromine atoms.

R$^2$ particularly preferably represents aryl having 6 to 10 carbon atoms, it being possible for each of these radicals to be monosubstituted to pentasubstituted by identical or different substituents consisting of fluorine, chlorine, bromine, iodine, cyano, nitro, in each case straight-chain or branched alkyl, alkoxy, or alkylsulphonyl having in each case 1 to 4 carbon atoms, in each case straight- chain or branched halogenoalkyl, halogenoalkoxy or halogenoalkylsulphonyl having in each case 1 to 4 carbon atoms and 1 to 9 identical or different halogen atoms, such as fluorine, chlorine and/or bromine, of straight-chain or branched alkoxycarbonyl having 1 to 4 carbon atoms in the alkoxy moiety, straight-chain or branched alkoximinoalkyl having 1 to 4 carbon atoms in the alkoxy moiety and 1 to 4 carbon atoms in the alkyl moiety, and/or of phenyl which in turn may be monosubstituted to trisubstituted by identical or different substituents consisting of fluorine, chlorine, bromine, straight-chain or branched alkyl or alkoxy having in each case 1 to 4 carbon atoms and/or straight-chain or branched halogenoalkyl or halogenoalkoxy having in each case 1 to 4 carbon atoms and 1 to 9 fluorine, chlorine and/or bromine atoms.

$R^1$ very particularly preferably represents 2-pyridyl, 3-pyridyl or 4-pyridyl, it being possible for each of these radicals to be monosubstituted or disubstituted by identical or different substituents consisting of fluorine, chlorine, bromine, cyano, nitro, methyl, ethyl, n-propyl, isopropyl, methoxy, ethoxy, methylsulphonyl, trifluoromethyl, trifluoromethoxy, trifluoromethylsulphonyl, methoxycarbonyl, methoximinomethyl and/or of phenyl which may in turn be monosubstituted or disubstituted by identical or different substituents consisting of fluorine, chlorine, methyl, ethyl, methoxy, trifluoromethyl or trifluoromethoxy.

$R^2$ very particularly preferably represents phenyl, α-naphthyl or β-naphthyl, it being possible for each of these radicals to be monosubstituted to trisubstituted by identical or different substituents consisting of fluorine, chlorine, bromine, cyano, nitro, methyl, ethyl, n- or isopropyl, n-, iso-, s- or t-butyl, methoxy, ethoxy, trifluoromethyl, difluoromethyl, trifluoromethoxy, difluoromethoxy, trifluoromethylsulphonyl, methoxycarbonyl, ethoxycarbonyl methoximinomethyl and/or of phenyl which may in turn be monosubstituted or disubstituted by identical or different substituents consisting of fluorine, chlorine, methyl, ethyl, methoxy, trifluoromethyl or trifluoromethoxy.

Preferred substances according to the invention are also addition products of acids and those pyridyl-1,2,4-thiadiazoles of the formula (I) in which $R^1$ and $R^2$ have the meanings indicated as preferable.

The acids which can be added on include, preferably, hydrohalic acids such as, for example, hydrochloric acid and hydrobromic acid, especially hydrochloric acid, and also phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and also sulphonic acids such as, for example, p-toluenesulphonic acid, 1,5-naphthalenedisulphonic acid or camphorsulphonic acid, saccharine and thiosaccharine.

Compounds which are furthermore preferred according to the invention are addition products of salts of metals from main groups II to IV and subgroups I and II and IV to VIII of the Periodic Table of the Elements and those pyridyl-1,2,4-thiadiazoles of the formula (I) in which $R^1$ and $R^2$ have the meanings indicated as preferable.

Particularly preferred salts in this context are those of copper, zinc, manganese, magnesium, tin, iron and nickel. Suitable anions of these salts are those derived from acids which lead to physiologically compatible addition products. Particularly preferred such acids in this context are the hydrohalic acids such as, for example, hydrochloric acid and hydrobromic acid, and also phosphoric acid, nitric acid and sulphuric acid.

Apart from the compounds mentioned in the preparation examples, specific mention may be made of the following pyridyl-1,2,4-thiadiazoles of the formula (I):

TABLE 1

TABLE 1-continued $$\underset{N\diagdown S}{\overset{R^1}{\underset{\|}{\diagup}}}\hspace{-2pt}\overset{N}{\underset{}{\diagdown}}\hspace{-6pt}-SO_2-CH_2-R^2 \qquad (I)$$

| R² | R¹ | R² | R¹ |
|---|---|---|---|
| 3-F-C₆H₄ | 3-pyridyl | 4-F-C₆H₄ | 3-pyridyl |
| 2,4-F₂-C₆H₃ | 3-pyridyl | 3,4-F₂-C₆H₃ | 3-pyridyl |
| 2-Br-C₆H₄ | 3-pyridyl | 3-Br-C₆H₄ | 3-pyridyl |
| 4-Br-C₆H₄ | 3-pyridyl | 2-CF₃-C₆H₄ | 3-pyridyl |
| 3-CF₃-C₆H₄ | 3-pyridyl | 4-CF₃-C₆H₄ | 3-pyridyl |
| 4-OCH₃-C₆H₄ | 3-pyridyl | 3-OCH₃-C₆H₄ | 3-pyridyl |
| 4-OC₂H₅-C₆H₄ | 3-pyridyl | 4-OC₂H₅-C₆H₄ | 2-pyridyl |
| 4-OC₂H₅-C₆H₄ | 4-pyridyl | 4-CH₃-C₆H₄ | 3-pyridyl |
| 2-CH₃-C₆H₄ | 3-pyridyl | 3-CH₃-C₆H₄ | 3-pyridyl |
| 2-C₂H₅-C₆H₄ | 3-pyridyl | 4-C₂H₅-C₆H₄ | 3-pyridyl |

TABLE 1-continued
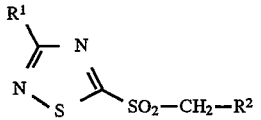

TABLE 1-continued
$$\text{(I)}$$
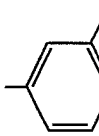
| R² | R¹ | R² | R¹ |
|---|---|---|---|
| 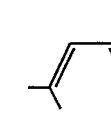 | 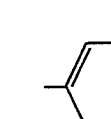 | 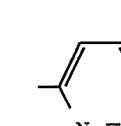 | 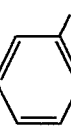 |
| 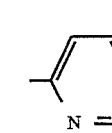 | 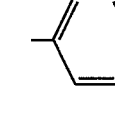 | 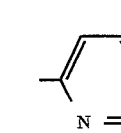 | 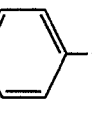 |
| 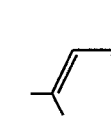 | 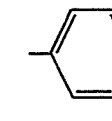 | 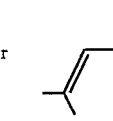 | 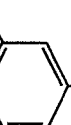 |
| 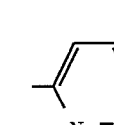 | 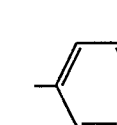 | 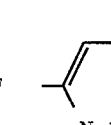 | 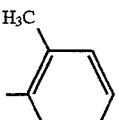 |
| 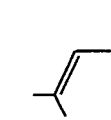 | 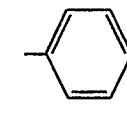 | 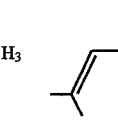 | 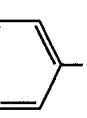 |
| 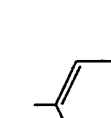 | 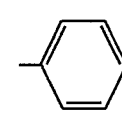 | 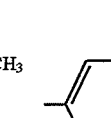 | 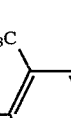 |
| 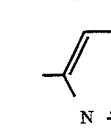 |  | 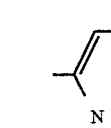 | 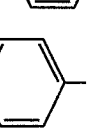 |
| 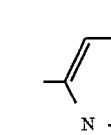 | 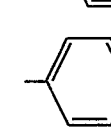 | 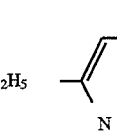 | 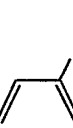 |
| 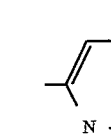 | 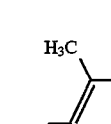 | 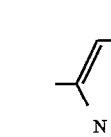 | |

TABLE 1-continued

Structure (I):

R¹—C(=N—S—N)—SO₂—CH₂—R²  (1,2,4-thiadiazole core)

| R² | R¹ | R² | R¹ |
|---|---|---|---|
| 2-Cl-phenyl | 6-Cl-pyridin-2-yl | 4-Cl-phenyl | 6-Cl-pyridin-2-yl |
| 3,4-diF-phenyl | 6-Cl-pyridin-2-yl | 2-OCH₃-phenyl | 6-Cl-pyridin-2-yl |
| 3,4-diF-phenyl | 6-F-pyridin-2-yl | 3-OCH₃-phenyl | 6-Cl-pyridin-2-yl |
| 3,4-diCl-phenyl | 6-F-pyridin-2-yl | 3,4-diCl-phenyl | 6-F-pyridin-2-yl |
| 3-CH₃-phenyl | 6-F-pyridin-2-yl | 4-C₂H₅-phenyl | 6-F-pyridin-2-yl |
| 3,5-diCH₃-phenyl | 6-F-pyridin-2-yl | 3-OCH₃-phenyl | 6-F-pyridin-2-yl |
| 4-OCH₃-phenyl | 6-F-pyridin-2-yl | 4-OC₂H₅-phenyl | 6-F-pyridin-2-yl |

Using, for example, 5-(4-bromobenzylthio)-3-(4-pyridyl)-1,2,4-thiadiazole as starting compound and potassium permanganate as oxidizing agent, the course of reaction of the process according to the invention can be represented by the following equation:

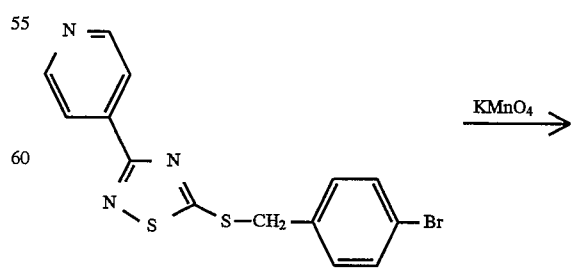

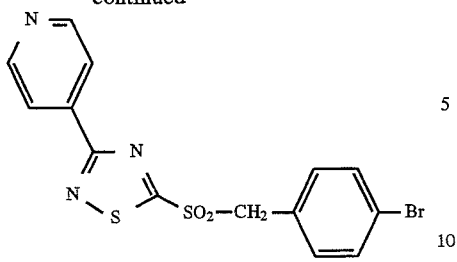

A general definition of the 5-arylalkylthio-1,2,4-thiadiazoles required as starting materials for carrying out the process according to the invention is given by the formula (II). In this formula (II), $R^1$ and $R^2$ preferably represent those radicals which have already been mentioned, in connection with the description of the compounds of the formula (I) according to the invention, as being preferable for these substituents.

The 5-arylalkylthio-1,2,4-thiadiazoles of the formula (II) have not yet been disclosed and are likewise a subject of the invention. They are obtained if 3-pyridyl-1,2,4-thiadiazoline-5-thiones of the formula

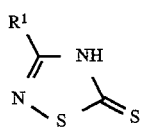
(III)

in which $R^1$ has the meaning given above are reacted with arylalkyl halides of the formula

$R^2$-CH$_2$-Hal (IV)

in which $R^2$ has the meaning given above and

Hal represents halogen, in particular chlorine or bromine, optionally in the presence of a diluent such as, for example, acetonitrile and optionally in the presence of a reaction auxiliary such as, for example, potassium carbonate, at temperatures of between 20° C. and 150° C.

3-Pyridyl-1,2,4-thiadiazoline-5-thiones of the formula (III) have likewise not yet been disclosed and are also a subject of the invention. They are obtained if pyridylamidine hydrochlorides of the formula

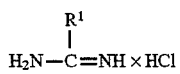
(V)

in which $R^1$ has the meaning given above are reacted with carbon disulphide in the presence of a diluent such as, for example, methanol and in the presence of a reaction auxiliary such as, for example, sodium methylate, and in the presence of a catalyst such as, for example, sulphur, at temperatures of between 20° C. and 150° C. (compare in this respect also the preparation examples).

Arylalkyl halides of the formula (IV) and pyridylamidine hydrochlorides of the formula (V) are generally known compounds of organic chemistry.

The compounds of the formula (III) may exist either as 3-pyridyl-1,2,4-thiadiazoline-5-thiones of the formula

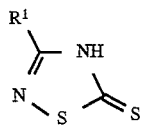
(III)

or in the form of their tautomers, the 3-pyridyl-5-mercapto-1,2,4-thiadiazoles of the formula

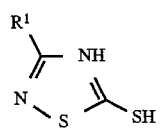
(IIIa)

In the reaction with arylalkyl halides of the formula (IV) it is the mercapto form of the formula (IIIa) which reacts.

The process according to the invention is carded out in the presence of a suitable oxidizing agent. Suitable such oxidizing agents are all those which can conventionally be used for sulphur oxidations. Preference is given to the use of hydrogen peroxide or organic peracids such as, for example, peracetic acid, 4-nitroperbenzoic acid or 3-chloroperbenzoic acid, or else inorganic oxidizing agents such as periodic acid, potassium permanganate or chromic acid.

Suitable diluents for carrying out the process according to the invention, depending on the oxidizing agent used, are inorganic or organic solvents. Preference is given to the use of alcohols such as methanol, ethanol, n- or isopropanol and their mixtures with water or pure water; furthermore, acids such as, for example, acetic acid, acetic anhydride or propionic acid, or dipolar aprotic solvents such as acetonitrile, acetone, ethyl acetate or dimethyl formamide, and also, if desired, halogenated hydrocarbons such as, for example, benzinc, benzene, toluene, xylene, chlorobenzene, dichlorobenzene, petroleum ether, hexane, cyclohexane, dichloromethane, dichloroethane, chloroform or carbon tetrachloride.

The process according to the invention can optionally also be carried out in the presence of a suitable acid-binding agent. Suitable such acid-binding agents are all conventional inorganic or organic bases. Preferred possibilities for use are alkaline earth metal, alkali metal or ammonium hydroxides, acetates, carbonates or hydrogen carbonates, such as, for example, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammoniumcarbonate.

The process according to the invention can optionally also be carried out in the presence of a suitable catalyst. Suitable such catalysts are all those which can conventionally be used for sulphur oxidations. Preference is given to the use of heavy metal catalysts. Those which can be mentioned by way of example in this context are ammonium molybdate or ammonium tungstate.

When carrying out the process according to the invention the reaction temperatures can be varied over a relatively wide range. The process is in general carried out at temperatures of between −30° C. and +150° C., preferably at temperatures of between 0° C. and 80° C.

The process according to the invention is usually carded out under atmospheric pressure. However, it is also possible to work under elevated or reduced pressure..

To carry out the process according to the invention, in general from 1.8 to 3.0 mol, preferably double-molar quantities, of oxidizing agent and, if appropriate, from 0.1 to 3.0 mol, preferably from 1.0 to 2.0 mol, of acid-binding agent and, if desired, from 0.001 to 2.0 mol, preferably from 0.01 to 1.0 mol, of catalysts are employed per mole of 5-arylalkylthio-1,2,4-thiadiazole of the formula (II). The implementation of the reaction and the working-up and isolation of the reaction products are carried out by generally known methods (cf. in this respect also the preparation examples).

The end products of the formula (I) are purified using conventional methods, for example by column chromatography or by recrystallization.

Characterization is made by means of the melting point or, in the case of compounds which do not crystallize, by means of the refractive index or of proton nuclear magnetic resonance spectroscopy ($^1$H-NMR).

The pyridyl-1,2,4-thiadiazoles of the formula (I) according to the invention can be converted to acid addition salts or metal salt complexes.

For the preparation of acid addition salts of the compounds of the formula (I), suitable acids are preferably those which have already been mentioned as preferred acids in connection with the description of the acid addition salts according to the invention..

The acid addition salts of the compounds of the formula (I) can be obtained in a simple manner by conventional methods of forming salts, for example by dissolving a compound of the formula (I) in a suitable inert solvent and adding the acid, for example hydrochloric acid, and can be isolated in a known manner, for example by filtration, and can be purified if desired by washing with an inert organic solvent.

To prepare metal salt complexes of the compounds of the formula (I), suitable metal salts are preferably those which have already been mentioned as preferred metal salts in connection with the description of the metal salt complexes according to the invention.

The metal salt complexes of the compounds of the formula (I) can be obtained in a simple manner by conventional methods, for example by dissolving the metal salt in alcohol, for example ethanol, and adding the solution to compounds of the formula (I). Metal salt complexes can be purified in a known manner, for example by filtration, isolation and, if desired, by recrystallization.

The active compounds according to the invention, and also the arylalkylthio-1,2,4-thiadiazoles of the formula (II), have a strong action against pests and can be employed in practice for combating unwanted harmful organisms. The active compounds are suitable for use as plant protection agents, especially as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum;* Phytophthora species, such as, for example, *Phytophthora infestans;* Pieudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *Peronospora brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *Pyrenophora graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context the active compounds according to the invention can be employed with particular success for combating diseases in fruit growing and vegetable cultivation, such as, for example, against the causative organism of apple scab (*Venturia inaequalis*) of against the causative organism of grapevine downy mildew (*Plasmopara viticola*) or for combating rice diseases such as, for example, against the causative organism of rice blast disease (*Pyricularia oryzae*).

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, and ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crashed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

When the substances according to the invention are employed, the application rate can be varied over a relatively wide range depending on the manner of application. Thus, in the treatment of parts of plants, the active compound concentrations in the use forms are, in general, between 1 and 0.0001% by weight, preferably between 0.5 and 0.001% by weight. In the treatment of seed, amounts of active compound of 0.001 to 50 g per kg of seed, preferably 0.1 to 10 g, are generally required. For the treatment of soil, active compound concentrations of 0.00001 to 0.1% by weight, preferably 0.0001 to 0.02%, are required at the place of action.

The preparation and use of the substances according to the invention is evident from the following examples.

PREPARATION EXAMPLES

EXAMPLE 1

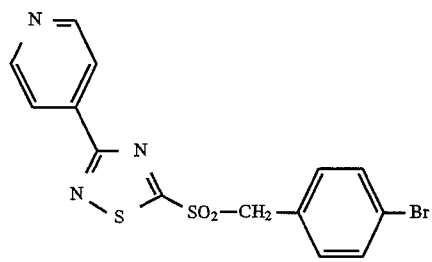

(I-1)

9.5 g (0.06 mol) of potassium permanganate are added to 10.9 g (0.03 mol) of 5-(4-bromobenzylthio)-3-(4-pyridyl)-1,2,4-thiadiazole in 75 ml of glacial acetic acid, and the mixture is subsequently stirred at from 50° to 60° C. for 16 hours. It is worked up by adding water, neutralizing the mixture with aqueous sodium hydroxide solution, breaking up precipitated manganese dioxide with aqueous sodium hydrogen sulphite solution, then extracting the mixture with dichloromethane, drying the combined organic phases over sodium sulphate, removing the solvent under reduced pressure, crystallizing the residue by stirring with ether, filtering off the crystals with suction and drying them.

4.7 g (40% of theory) are obtained of 5-(4-bromobenzylsulphonyl)-3-(4-pyridyl)-1,2,4-thiadiazole of melting point 173° C.

PREPARATION OF THE STARTING COMPOUNDS

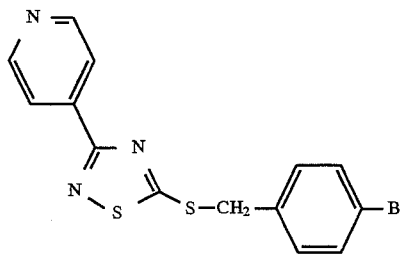

(II-1)

9.8 g (0.05 mol) of 5-mercapto-3-(4-pyridyl)-1,2,4-thiadiazole together with 13.8 g (0.055 mol) of 4-bromobenzyl bromide and 8.3 g (0.06 mol) of potassium carbonate in 100 ml of acetonitrile are heated at reflux temperature for 16 hours. The mixture is worked up by concentrating it in vacuo, taking up the residue in dichloromethane, washing it with water, drying it over sodium sulphate and then concentrating the mixture in vacuo. The residue is crystallized by stirring with ether, and the crystals are filtered off with suction and dried.

7.8 g (43% of theory) are obtained of 5-(4-bromobenzylthio)-3-(4-pyridyl)-1,2,4-thiadiazole of melting point 132° C.

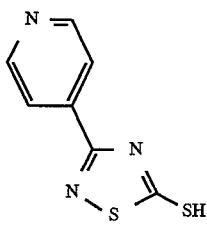

(III-1)

315 g (2.0 mol) of 4-pyridylamidine hydrochloride, 1380 g (6.0 mol) of 30% strength sodium methylate solution in methanol, 380 g (5.0 mol) of carbon disulphide and 83.2 g (2.6 mol) of sulphur powder are heated in 2000 ml of methanol at reflux temperature for 16 hours, and the mixture is then cooled to room temperature. The reaction mixture is worked up by concentrating it in vacuo. The residue is dissolved in hot water and the solution is filtered. The filtrate is adjusted to a pH of 4 with acetic acid. Precipitated solid is filtered off with suction and suspended in hot isopropanol, and the suspension is cooled again, and the solid is filtered off with suction and dried.

259 g (66% of theory) are obtained of 5-mercapto-3-(4-pyridyl)-1,2,4-thiadiazole of melting point 206° C. (decomposition).

In a corresponding manner, and in accordance with the general instructions for preparation, the following pyridyl-1,2,4-thiadiazoles are obtained of the formula (I):

TABLE 2

| Example Number | Compd. No. | $R^1$ | $R^2$ | physical properties |
|---|---|---|---|---|
| 2 | I-2 | 4-pyridyl | 4-Cl-phenyl | m.p. 146° C. |
| 3 | I-3 | 4-pyridyl | 4-CF$_3$-phenyl | m.p. 131° C. |
| 4 | I-4 | 4-pyridyl | 2-Cl-phenyl | m.p. 139° C. |
| 5 | I-5 | 3-pyridyl | 4-CH$_3$-phenyl | m.p. 114° C. |
| 6 | I-6 | 3-pyridyl | 2,4-di-Cl-phenyl | m.p. 153° C. |
| 7 | I-7 | 3-pyridyl | naphthyl | m.p. 137° C. |
| 8 | I-8 | 3-pyridyl | 3-CF$_3$-phenyl | m.p. 171° C. |
| 9 | I-9 | 3-pyridyl | 4-C$_2$H$_5$-phenyl | $^1$H-NMR*): 4.75 (s, 2H) |

TABLE 2-continued $$\text{(I)}$$

General structure: R¹ attached to a thiadiazole ring with SO₂—CH₂—R² substituent.

| Example Number | Compd. No. | R¹ | R² | physical properties |
|---|---|---|---|---|
| 10 | I-10 | 4-pyridyl | 2,4-difluorophenyl | m.p. 115° C. |
| 11 | I-11 | 4-pyridyl | 3-(trifluoromethyl)phenyl | m.p. 89° C. |
| 12 | I-12 | 4-pyridyl | 2-(trifluoromethyl)phenyl | m.p. 135° C. |
| 13 | I-13 | 4-pyridyl | 2-methylphenyl | m.p. 128° C. |
| 14 | I-14 | 4-pyridyl | 4-methoxyphenyl | m.p. 143° C. |
| 15 | I-15 | 4-pyridyl | 2-bromophenyl | ¹H-NMR*): 8.1 (d, 2H; J = 8 Hz) |
| 16 | I-16 | 2-pyridyl | 4-fluorophenyl | m.p. 126° C. |
| 17 | I-17 | 2-pyridyl | 1-naphthyl | m.p. 126° C. |
| 18 | I-18 | 2-pyridyl | 2,4-difluorophenyl | m.p. 169° C. |
| 19 | I-19 | 2-pyridyl | 2-(trifluoromethyl)phenyl | m.p. 120° C. |

TABLE 2-continued $$\underset{N\diagdown S}{\overset{R^1}{\diagup}}\diagdown\overset{N}{\diagdown}SO_2-CH_2-R^2 \qquad (I)$$

| Example Number | Compd. No. | R¹ | R² | physical properties |
|---|---|---|---|---|
| 20 | I-20 | 3-pyridyl | 2-Cl-phenyl | m.p. 108° C. |
| 21 | I-21 | 2-pyridyl | 3-CH₃-phenyl | m.p. 141° C. |
| 22 | I-22 | 2-pyridyl | 2,4-(CH₃)₂-phenyl | m.p. 145° C. |
| 23 | I-23 | 4-pyridyl | 3,4-F₂-phenyl | m.p. 130° C. |
| 24 | I-24 | 2-pyridyl | 2-F-6-Cl-phenyl | m.p. 145° C. |
| 25 | I-25 | 2-pyridyl | 2-CF₃-phenyl | m.p. 147° C. |
| 26 | I-26 | 2-pyridyl | 4-C₂H₅-phenyl | ¹H-NMR*⁾: 4.8 (s, 2H) |
| 27 | I-27 | 3-pyridyl | 4-Cl-phenyl | m.p. 108° C. |
| 28 | I-28 | 3-pyridyl | 3,4-Cl₂-phenyl | m.p. 105° C. |
| 29 | I-29 | 3-pyridyl | 2,4-F₂-phenyl | m.p. 127° C. |

TABLE 2-continued $$\text{(I)}$$

Structure: R¹ group attached to a 1,2,4-thiadiazole ring (N=C(R¹)-N=C(SO₂—CH₂—R²)-S-) with SO₂—CH₂—R² substituent.

| Example Number | Compd. No. | R¹ | R² | physical properties |
|---|---|---|---|---|
| 30 | I-30 | 3-pyridyl | 1-methylnaphthalen-? yl 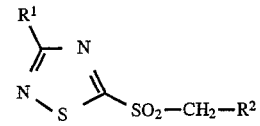 | m.p. 147° C. |
| 31 | I-31 | 3-pyridyl | 3,5-dichlorophenyl 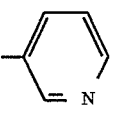 | m.p. 149° C. |
| 32 | I-32 | 3-pyridyl | 3-(trifluoromethyl)phenyl 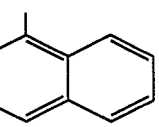 | m.p. 139° C. |
| 33 | I-33 | 3-pyridyl | 2-fluorophenyl 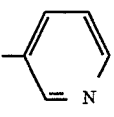 | m.p. 108° C. |
| 34 | I-34 | 3-pyridyl | 4-fluorophenyl 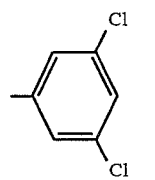 | m.p. 137° C. |
| 35 | I-35 | 3-pyridyl | 2,4-dichlorophenyl 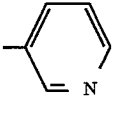 | m.p. 117° C. |
| 36 | I-36 | 3-pyridyl | 3-bromophenyl 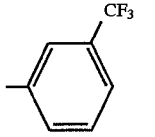 | m.p. 165° C. |
| 37 | I-37 | 2-pyridyl | 2-bromophenyl 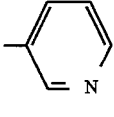 | m.p. 124° C. |
| 38 | I-38 | 2-pyridyl | 3-fluorophenyl 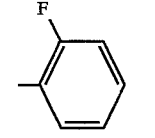 | m.p. 95–100° C. |
| 39 | I-39 | 2-pyridyl | 4-methoxyphenyl 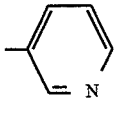 | m.p. 156° C. |

TABLE 2-continued

Structure (I): R¹-C(=N-N=C(-S-)-SO₂-CH₂-R²) (1,3,4-thiadiazole)

| Example Number | Compd. No. | R¹ | R² | physical properties |
|---|---|---|---|---|
| 40 | I-40 | 3-pyridyl | 3,4-difluorophenyl | m.p. 147° C. |
| 41 | I-41 | 3-pyridyl | 4-(CF₃)phenyl | m.p. 129° C. |
| 42 | I-42 | 3-pyridyl | 4-bromophenyl | m.p. 122° C. |
| 43 | I-43 | 3-pyridyl | 3-methoxyphenyl | m.p. 97° C. |
| 44 | I-44 | 3-pyridyl | 4-methylphenyl | m.p. 149° C. |
| 45 | I-45 | 2-pyridyl | 3-fluorophenyl | m.p. 152° C. |
| 46 | I-46 | 2,6-dimethyl-4-pyridyl | 4-chlorophenyl | m.p. 176° C. |
| 47 | I-47 | 2,6-dimethyl-4-pyridyl | 2,4-difluorophenyl | oil |
| 48 | I-48 | 2,6-dimethyl-4-pyridyl | 2-fluorophenyl | m.p. 176° C. |

TABLE 2-continued $$\underset{\text{N}\underset{\text{S}}{\diagdown}}{\overset{R^1}{\diagup}}\!\!\!\!\!\overset{\text{N}}{\diagdown}\!\!\!\!\!\underset{\text{SO}_2\text{—CH}_2\text{—R}^2}{\diagup} \quad (I)$$

| Example Number | Compd. No. | R¹ | R² | physical properties |
|---|---|---|---|---|
| 49 | I-49 | 2,6-dimethylpyridin-4-yl | 4-fluorophenyl | m.p. 143° C. |
| 50 | I-50 | 2,6-dimethylpyridin-4-yl | 2-methylphenyl | m.p. 107° C. |
| 51 | I-51 | pyridin-2-yl | 3-bromophenyl | m.p. 140° C. |

*)The ¹H-NMR spectra were recorded in deuterochloroform (CDCl₃) or hexadeutero-dimethyl sulphoxide (DMSO-d₆) with tetramethylsilane (TMS) as internal standard. The value given is the chemical shift d in ppm.

The starting substances of the formula (III) indicated in the following examples are also prepared by the method indicated in Example 1.

EXAMPLE 52

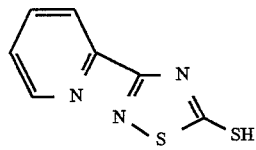

III-2

5-Mercapto-3-(2-pyridyl)-1,2,4-thiadiazole Yield: 178.5 g (46% of theory) Melting point: 197° C.

EXAMPLE 53

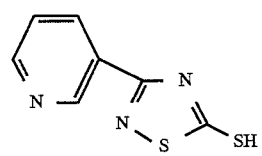

III-3

5-Mercapto-3-(3-pyridyl)-1,2,4-thiadiazole Yield: 289 g (74% of theory) Melting point: 203° C. (decomposition)

USE EXAMPLES

In the following use examples, the compounds listed below were employed as comparison substances:

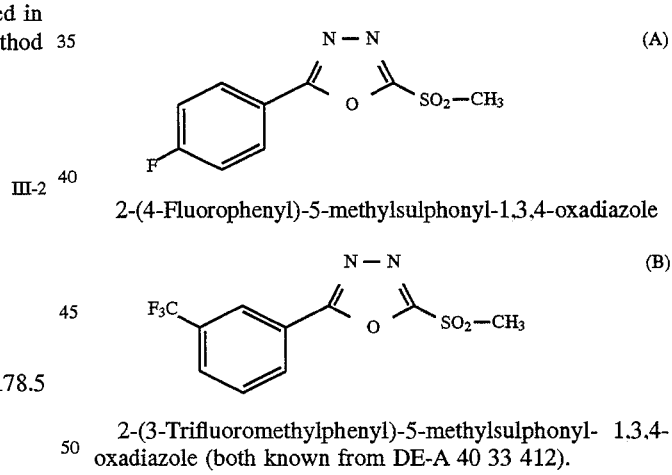

2-(4-Fluorophenyl)-5-methylsulphonyl-1,3,4-oxadiazole 2-(3-Trifluoromethylphenyl)-5-methylsulphonyl-1,3,4-oxadiazole (both known from DE-A 40 33 412).

EXAMPLE A

Venturia test (apple)/protective

Solvent: 4.7 parts by weight of acetone

Emulsifier: 0.3 parts by weight of alkyl-aryl polyglycol ether

To produce a suitable preparation of active compound, one part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for one day.

The plants are then placed in a greenhouse at 20° C. and a relative atmospheric humidity of about 70%.

Evaluation is carried out 12 days after the inoculation.

In this test the substances according to the invention indicated in Examples 2, 3, 4, 7, 8, 10, 11, 16, 24 and 25 display a degree of action, at an active compound concentration of 10 ppm in the spray liquid, of more than 70%, whereas the degree of action of the comparison substances (A) and (B) is only 3 and 0% respectively.

EXAMPLE B

Piasmo para test (vines)/protective

Solvent: 4.7 parts by weight of acetone

Emulsifier: 0.3 parts by weight of alkyl-aryl polyglycol ether

To produce a suitable preparation of active compound, one part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Plasmopara viticola and then remain in a humidity chamber at 20° to 22° C. and 100% relative atmospheric humidity for one day. The plants are then placed in a greenhouse at 21° C. and 90% atmospheric humidity for 5 days. The plants are then moistened and placed in a humidity chamber for one day.

Evaluation is carried out 6 days after the inoculation.

In this test the substances according to the invention indicated in Examples 1, 2, 5, 10, 13, 15, 17, 18, 19, 24 and 26 display a degree of action, at an active compound concentration of 10 ppm in the spray liquid, of more than 80%, whereas the degree of action of the comparison substances (A) and (B) is 0.

We claim:

1. A method of combating fungi which comprises applying to such fungi or to a locus from which it is desired to exclude such fungi a fungicidally effective amount of a compound or salt of a pyridyl-1,2,4-thiadiazole of the formula

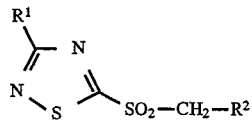
(I)

in which $R^1$ represents 2-pyridyl, 3-pyridyl or 4-pyridyl, it being possible for each of these radicals to be monosubstituted to tetrasubstituted by identical or different substituents consisting of halogen, cyano, nitro, in each case straight-chain or branched alkyl, alkoxy or alkylsulphonyl having in each case 1 to 6 carbon atoms, in each case straight-chain or branched halogenoalkyl, halogenoalkoxy or halogenoalkylsulphonyl having in each case 1 to 6 carbon atoms and 1 to 13 identical or different halogen atoms, straight-chain or branched alkoxycarbonyl having 1 to 6 carbon atoms in the alkoxy group, straight-chain or branched alkoximinoalkyl having 1 to 6 carbon atoms in the alkoxy moiety and 1 to 6 carbon atoms in the alkyl moiety, and of phenyl which in turn may be monosubstituted to tetrasubstituted by identical or different substituents consisting of halogen and/or straight-chain or branched alkyl or alkoxy having in each case 1 to 6 carbon atoms and/or straight-chain or branched halogenoalkyl or halogenoalkoxy having in each case 1 to 6 carbon atoms and 1 to 13 identical or different halogen atoms, and $R^2$ represents aryl having 6 to 10 carbon atoms, it being possible for each of these radicals to be monosubstituted to pentasubstituted by identical or different substituents consisting of halogen, cyano, nitro, in each case straight-chain or branched alkyl, alkoxy or alkylsulphonyl having in each case 1 to 6 carbon atoms, in each case straight-chain or branched halogenoalkyl, halogenoalkoxy or halogenoalkylsulphonyl having in each case 1 to 6 carbon atoms and 1 to 13 identical or different halogen atoms, straight-chain or branched alkoxycarbonyl having 1 to 6 carbon atoms in the alkoxy group, straight-chain or branched alkoximinoalkyl having 1 to 6 carbon atoms in the alkoxy moiety and 1 to 6 carbon atoms in the alkyl moiety, and of phenyl which in turn may be monosubstituted to pentasubstituted by identical or different substituents consisting of halogen and/or straight-chain or branched alkyl or alkoxy having in each case 1 to 6 carbon atoms and/or straight-chain or branched halogenoalkyl or halogenoalkoxy having in each case 1 to 6 carbon atoms and 1 to 13 identical or different halogen atoms.

* * * * *